(12) United States Patent
Schmidt

(10) Patent No.: US 10,104,223 B2
(45) Date of Patent: Oct. 16, 2018

(54) AUTOMATICALLY APPLYING MODIFICATIONS TO A DEVICE IN A LIQUID ENVIRONMENT

(71) Applicant: Motorola Mobility LLC, Chicago, IL (US)

(72) Inventor: Dave J Schmidt, Mundelein, IL (US)

(73) Assignee: Motorola Mobility LLC, Chicago, IL (US)

(*) Notice: Subject to any disclaimer, the term of this patent is extended or adjusted under 35 U.S.C. 154(b) by 23 days.

(21) Appl. No.: 14/992,096

(22) Filed: Jan. 11, 2016

(65) Prior Publication Data
US 2017/0201618 A1 Jul. 13, 2017

(51) Int. Cl.
G08B 21/00 (2006.01)
H04M 1/725 (2006.01)
G01N 27/02 (2006.01)
H04L 12/26 (2006.01)
H04W 8/22 (2009.01)
H04M 1/18 (2006.01)

(52) U.S. Cl.
CPC ........ H04M 1/72569 (2013.01); G01N 27/02 (2013.01); H04L 43/16 (2013.01); H04W 8/22 (2013.01); H04M 1/18 (2013.01)

(58) Field of Classification Search
CPC .......................... H04M 1/72569; G01N 27/02
USPC ........................................................ 340/620
See application file for complete search history.

(56) References Cited

U.S. PATENT DOCUMENTS

| | | | |
|---|---|---|---|
| 3,320,018 A * | 5/1967 | Pepke | G03B 17/08 351/43 |
| 6,795,110 B1 * | 9/2004 | Kossin | H04N 5/2252 348/164 |
| 7,908,921 B2 * | 3/2011 | Binda | G01C 5/06 73/384 |
| 9,574,877 B2 * | 2/2017 | Sasaki | G01C 5/06 |
| 2002/0003584 A1 * | 1/2002 | Kossin | H04N 5/2252 348/373 |
| 2008/0028852 A1 * | 2/2008 | Dwyer | G01F 23/247 73/295 |
| 2011/0018728 A1 * | 1/2011 | Uhlhorn | A47L 15/4297 340/657 |
| 2011/0211061 A1 * | 9/2011 | Kossin | H04N 5/2252 348/81 |

(Continued)

OTHER PUBLICATIONS

Dean E. Thorson, et al., "Systems and Method for Managing Operating Modes of an Electronic Device", U.S. Appl. No. 14/229,052, filed Mar. 28, 2014.

*Primary Examiner* — Julie Lieu
(74) *Attorney, Agent, or Firm* — Yudell Isidore PLLC (57) ABSTRACT

A method, a system, and computer program product automatically apply at least one modification to a device that optimizes the operation of the device in a liquid environment. The method includes detecting immersion of a device in a liquid environment. In response to determining the device is immersed in the liquid environment, at least one modification is determined that can be applied to the device to enable specific device functionality while the device is immersed in the liquid environment. The at least one modification is then applied to the device. In response to detecting that the device is no longer immersed in the liquid environment, the at least one modification to the device is reverted.

18 Claims, 7 Drawing Sheets

(56) References Cited

U.S. PATENT DOCUMENTS

| | | | |
|---|---|---|---|
| 2012/0281944 A1* | 11/2012 | Yang | H04B 10/0771 |
| | | | 385/12 |
| 2012/0325022 A1* | 12/2012 | Shanebrook | G01F 23/16 |
| | | | 73/862.581 |
| 2014/0216711 A1* | 8/2014 | Shelnutt | F28D 15/0266 |
| | | | 165/301 |
| 2015/0060009 A1* | 3/2015 | Shelnutt | F28F 27/02 |
| | | | 165/11.1 |
| 2015/0179037 A1* | 6/2015 | Ren | G01L 7/18 |
| | | | 340/522 |
| 2016/0051169 A1* | 2/2016 | Hong | A63B 71/06 |
| | | | 600/595 |
| 2016/0146935 A1* | 5/2016 | Lee | G01S 15/02 |
| | | | 367/87 |
| 2017/0010691 A1* | 1/2017 | Morobishi | G06F 3/044 |
| 2017/0011507 A1* | 1/2017 | Wong | G01N 21/896 |
| 2017/0085771 A1* | 3/2017 | Schwager | G01S 13/867 |

\* cited by examiner

AUTOMATICALLY APPLYING MODIFICATIONS TO A DEVICE IN A LIQUID ENVIRONMENT

BACKGROUND

1. Technical Field

The present disclosure generally relates to electronic devices and in particular to an improved method for automatically modifying the operation of an electronic device in response to detecting immersion of the device in a liquid environment.

2. Description of the Related Art

Electronic devices, such as a mobile device, can be harmed if immersed in a liquid environment, due in part to ingress of the liquid into the device. Due to the wide usage of most devices outside of a liquid environment, a vast majority of mobile devices are configured primarily for operation outside of a liquid environment and users are cautioned against submersion of these devices. Solutions currently exist to protect some devices from harm when immersed. However, even for mobile devices that are designed to not be damaged by immersion in a liquid, some components of a mobile device, when used in a liquid environment, may be subject to conditions that adversely affect the operation and/or performance of the mobile device. For example, touch screen displays may become less responsive or unresponsive when immersed in a liquid environment. Additionally, due to the increased density of a liquid environment, wireless radios may have increased difficulty maintaining wireless connections to other devices while submerged.

BRIEF DESCRIPTION OF THE DRAWINGS

The description of the illustrative embodiments is to be read in conjunction with the accompanying drawings, wherein.

DETAILED DESCRIPTION

The illustrative embodiments provide a method, a system, and a computer program product for automatically applying at least one modification to an electronic device to enable specific device functionality while the device is immersed in a liquid environment. The method includes detecting immersion of the device in the liquid environment. The method further includes, in response to determining the device is immersed in the liquid environment, automatically determining at least one modification that can be applied to the device to enable specific device functionality while immersed in the liquid environment. The at least one modification is then applied to the device. In response to detecting that the device is no longer immersed in the liquid environment, the at least one modification to the device is reverted.

The above contains simplifications, generalizations and omissions of detail and is not intended as a comprehensive description of the claimed subject matter but, rather, is intended to provide a brief overview of some of the functionality associated therewith. Other systems, methods, functionality, features, and advantages of the claimed subject matter will be or will become apparent to one with skill in the art upon examination of the following figures and the remaining detailed written description. The above as well as additional objectives, features, and advantages of the present disclosure will become apparent in the following description.

In the following detailed description, specific example embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various aspects are described which may be aspects for some embodiments but not other embodiments.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Moreover, the use of the terms first, second, etc. do not denote any order or importance, but rather the terms first, second, etc. are used to distinguish one element from another.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be provided its broadest interpretation given the context in which that term is utilized.

As utilized herein, immersion refers to the submersion of a device under a surface of a liquid. The immersion may be a total or partial submersion of the device in a liquid. The liquid may be, for example, salt water, fresh water, or any other aqueous solution.

Figure 1:
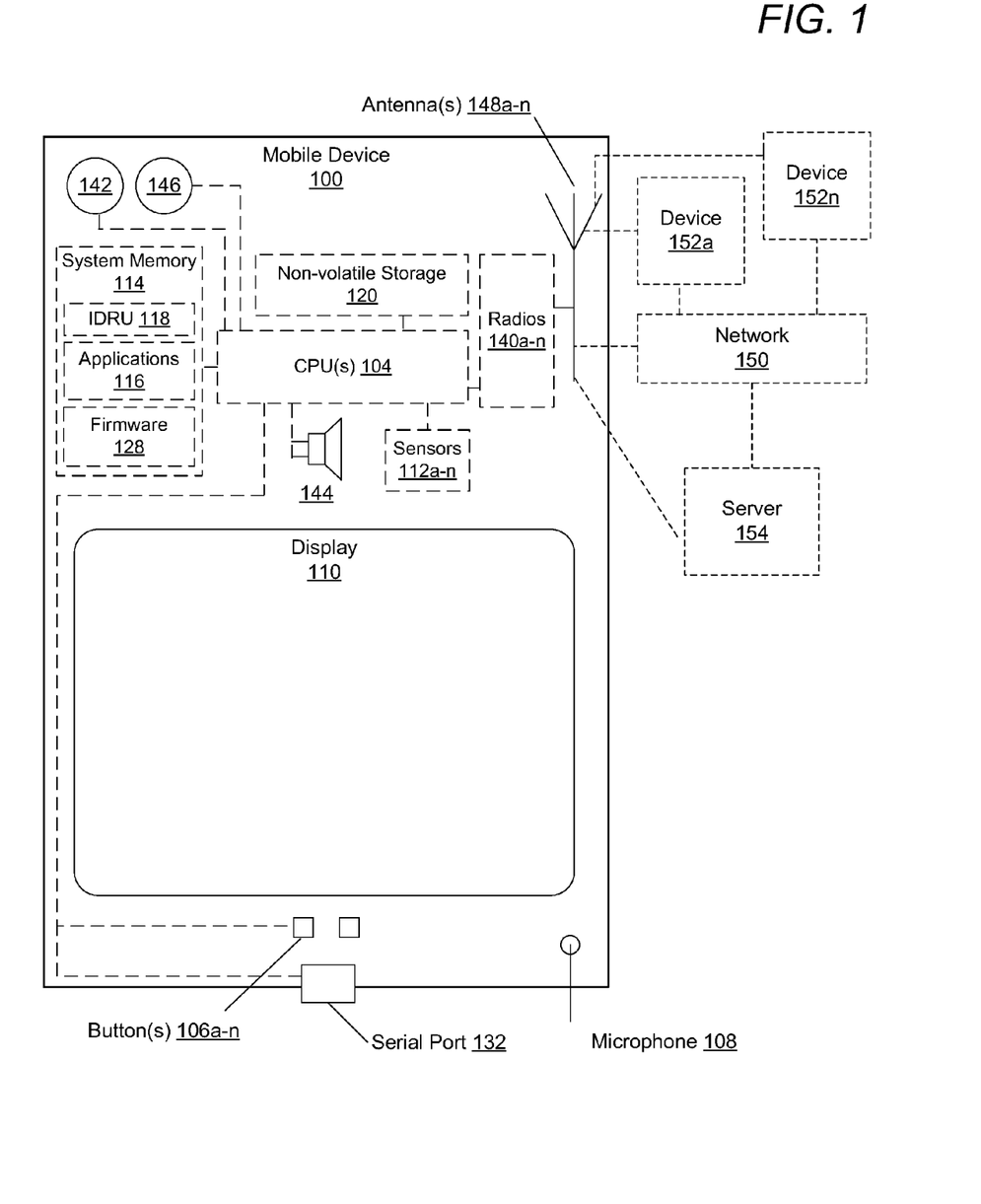
FIG. 1 provides a block diagram representation of a mobile device within which certain aspects of the disclosure can be practiced, in accordance with one or more embodiments.

Those of ordinary skill in the art will appreciate that the hardware components and basic configuration depicted in the following figures may vary. For example, the illustrative components within device 100 are not intended to be exhaustive, but rather are representative to highlight components that are utilized to implement the present disclosure. For example, other devices/components may be used in addition to or in place of the hardware depicted. The depicted example is not meant to imply architectural or other limitations with respect to the presently described embodiments and/or the general disclosure.

Within the descriptions of the different views of the figures, the use of the same reference numerals and/or symbols in different drawings indicates similar or identical items, and similar elements can be provided similar names and reference numerals throughout the figure(s). The specific identifiers/names and reference numerals assigned to the elements are provided solely to aid in the description and are not meant to imply any limitations (structural or functional or otherwise) on the described embodiments.

With reference now to the figures, and beginning with FIG. 1, there is depicted a block diagram representation of an example mobile device 100, within which one or more of the described features of the various embodiments of the disclosure can be implemented. In one embodiment, mobile device 100 can be any portable electronic device such as a notebook computer, health and/or fitness monitoring device, mobile phone, watch, smart watch, camera, video recorder, or tablet.

Mobile device 100 includes at least one central processing unit (CPU) or processor 104. CPU 104 is coupled to system memory 114 and/or non-volatile storage 120, within which firmware 128, applications 116, and immersion detection and response utility (IDRU) 118 can be stored for execution on CPU 104. IDRU 118 executes within mobile device 100 to provide logic that performs the various methods and functions described herein. For simplicity, IDRU 118 is illustrated and described as a stand-alone or separate software/firmware/logic component, which provides the specific functions and methods described below. However, in at least one embodiment, IDRU 118 may be a component of, may be combined with, or may be incorporated within firmware 128 of mobile device 100, or within an operating system (not pictured) and/or one or more applications 116.

As shown, mobile device 100 comprises several input devices and output devices for interacting with a user. In the illustrated embodiment, mobile device 100 includes a camera sensor 142, camera flash 146, hardware buttons 106a-n, microphone 108, and speaker 144. Camera flash 146 may be used in conjunction with camera sensors 142 in order to capture image data. Microphone 108 may be used to receive spoken input/commands from a user, and/or ambient sound. Speaker 144 is used to output audio. Hardware buttons 106a-n are selectable buttons which are used to receive manual/tactile input from a user to control specific operations of mobile device and/or of device applications. In one embodiment, hardware buttons 106a-n may also include or be connected to one or more sensors (e.g. a fingerprint scanner) and/or be pressure sensitive. Hardware buttons 106a-n may also be directly associated with one or more functions of the GUI and/or functions of an OS, application, or hardware of mobile device 100. In one embodiment, hardware buttons 106a-n may include a keyboard.

Mobile device 100 also includes serial port 132 (e.g. a micro-USB (universal serial bus) port) which is one of an input port, an output port, and an input/output port that allows a direct physical connection to and communication of data with a second device. In one embodiment, serial port 132 may also connect to a power charger (not pictured) for charging a battery (not pictured) of mobile device 100. In another embodiment, serial port 132 is a two-pin port.

Mobile device 100 also includes a display 110 that is capable of displaying a graphical user interface (GUI) of firmware and/or one or more applications executing on mobile device 100. In one embodiment, display 110 is a touch screen that is also capable of receiving touch input from a user of mobile device 100 interacting with a displayed GUI. A GUI displayed by mobile device 100 on display 110 may be rendered by CPU 104 and/or optionally by a graphical processing unit (GPU), if present. Mobile device 100 also includes one or more wireless radios 140a-n and one or more antenna(s) 148a-n that enable mobile device 100 to wirelessly connect to, and transmit and receive data with one or more other devices, such as devices 152a-n and server 154. As a wireless device, mobile device 100 can transmit the data over a wireless network 150 (e.g., a Wi-Fi network, cellular network, Bluetooth network, or personal area network).

Mobile device 100 also includes sensors 112a-n. Sensors 112a-n may include liquid detection sensors for detecting the immersion of mobile device 100 in a liquid. In one embodiment, mobile device 100 may include multiple liquid detection sensors located at different areas (e.g., at opposite ends) of device 100 in order to detect a partial immersion of mobile device 100 in a liquid. Sensors 112a-n may also include a barometric altimeter for determining a barometric pressure of a current environment. In another embodiment, sensors 112a-n may further include an infrared (IR) sensors, ambient light sensors, proximity sensors, temperature sensors, and sensors used for detecting motion, including, but not limited to, gyroscopic sensors, accelerometers, and magnetometers. In still another embodiment, sensors 112a-n may include sensors for identifying a current location of mobile device, such as a global positioning satellite (GPS) sensor.

Figure 2:
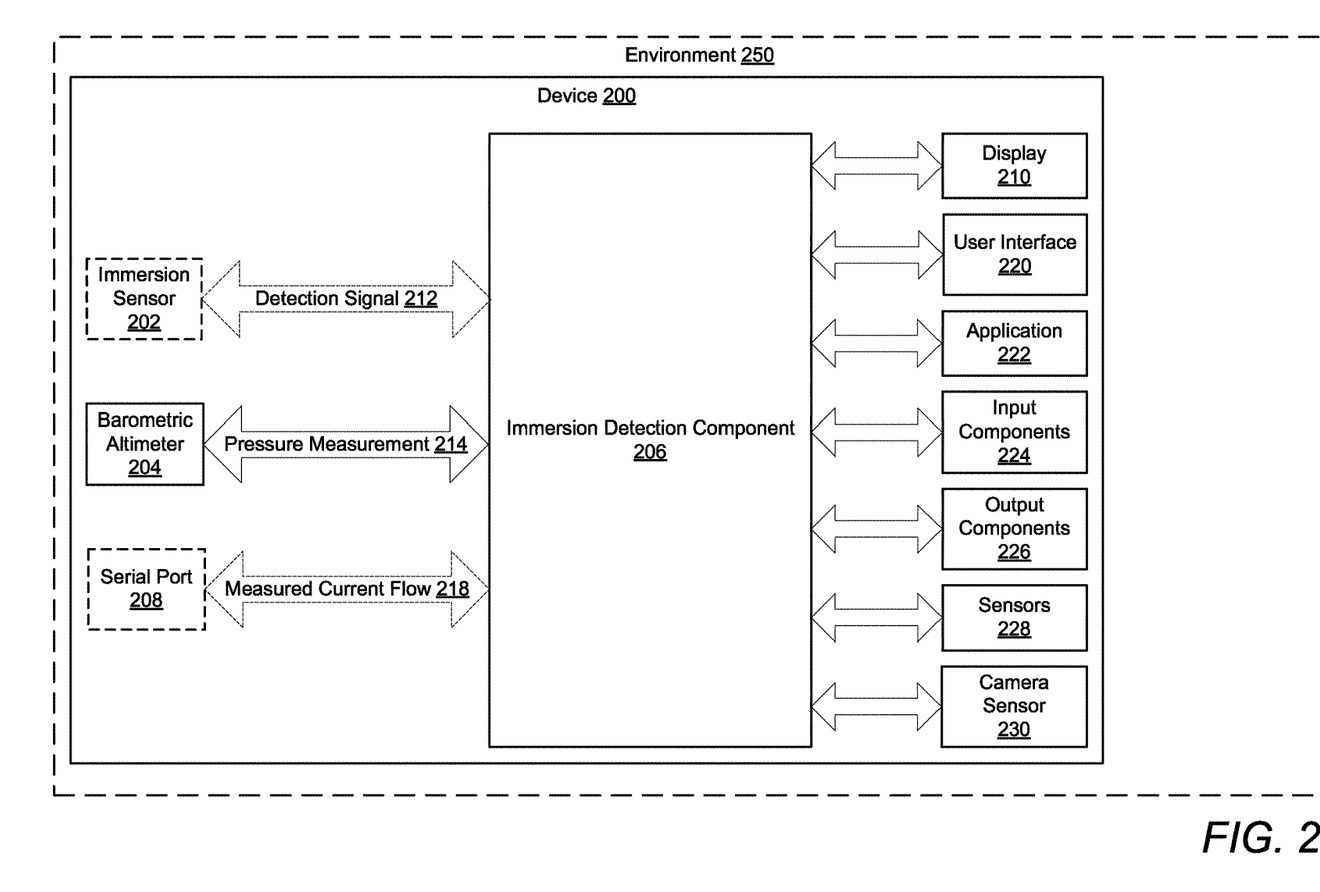
FIG. 2 illustrates a device having an immersion detection component that, in response to determining the device is immersed in a liquid, automatically determines and applies at least one modification to the mobile device that enables specific device functionality while immersed in the liquid environment, in accordance with one or more embodiments.

FIG. 2 illustrates an example device 200 having an immersion detection component (IDC) 206 that, in response to determining that device 200 is immersed in a liquid environment, autonomously determines and applies at least one modification to device 200 that enables specific device functionality while immersed in the liquid environment, in accordance with one or more embodiments. The specific device functionality optimizes the operation of the device in the liquid environment and/or modifies operations of device 200 based on hardware limitations of device 200 and/or characteristics of the environment 250. IDC 206 includes a processor that executes IDRU 118. In one embodiment, device 200 is a mobile device such as mobile device 100.

In one embodiment, the particular modifications that IDC 206 applies to the device in response to determining the device is immersed in a liquid environment are predetermined. In another embodiment, the particular modifications that IDC 206 applies to the device in response to determining the device is immersed in a liquid environment may be automatically selected by IDC 206 based on one or more of: a type of liquid environment; a temperature of the liquid environment; a depth of the device in the liquid environment; a remaining charge of a battery of device 200; an amount of time that the device has been immersed in the liquid environment; and a hardware and/or software configuration of device 200.

In one embodiment, device 200 includes at least one of an immersion sensor 202 coupled to IDC 206. Accordingly, IDC 206 receives detection signal 212 from immersion sensor 202 which indicates whether device 200 is immersed in a liquid. In one embodiment, immersion sensor 202 is a dedicated sensor for detecting immersion of device 200 in a liquid environment. In another embodiment, the functionality of immersion sensor 202 is provided by another sensor (e.g., a touch screen display) within device 200 that is also capable of detecting when device 200 is immersed in a liquid environment. In still another embodiment, immersion sensor 202 is included within immersion detection component 206.

In yet another embodiment, IDC 206 may analyze and correlate data captured by a combination of sensors to determine whether device 200 is immersed in a liquid. That data may include, for example: (1) characteristics of an audio recording that was recorded using a microphone of device 200, (2) characteristics and/or change in a measured wireless signal by a wireless radio of device 200, (3) characteristics measured by an ambient light sensor of device 200, (4) a measured sudden change in a pressure measurement of environment 250.

In still another embodiment, IDC 206 may repurpose serial port 208 of device 200 to determine whether device 200 is immersed in a liquid environment. In order to detect whether device 200 is immersed in a liquid environment using serial port 208, IDC 206 applies a voltage to a first pin of serial port 208. IDC 206 then measures a current flow 218 between the first pin and a second pin of serial port 208. Based on the measured current flow 218 between the first pin and the second pin of serial port 208, IDC 206 calculates a level of electrical conductivity of environment 250. The calculated level of electrical conductivity of environment 250 is then compared to a plurality of known electrical conductivity values that are stored in a table within device 200 and/or are otherwise accessible by device 200. In one embodiment, the plurality of known electrical conductivity values may include electrical conductivity values for a variety of environments including, but not limited to, air, salt water, and fresh water. IDC 206 then determines, based on the calculated level of electrical conductivity of environment 250, whether environment 250 is a liquid environment, and can also determine a specific type and/or characteristics of a liquid environment based on the electrical conductivity values.

Figure 5:
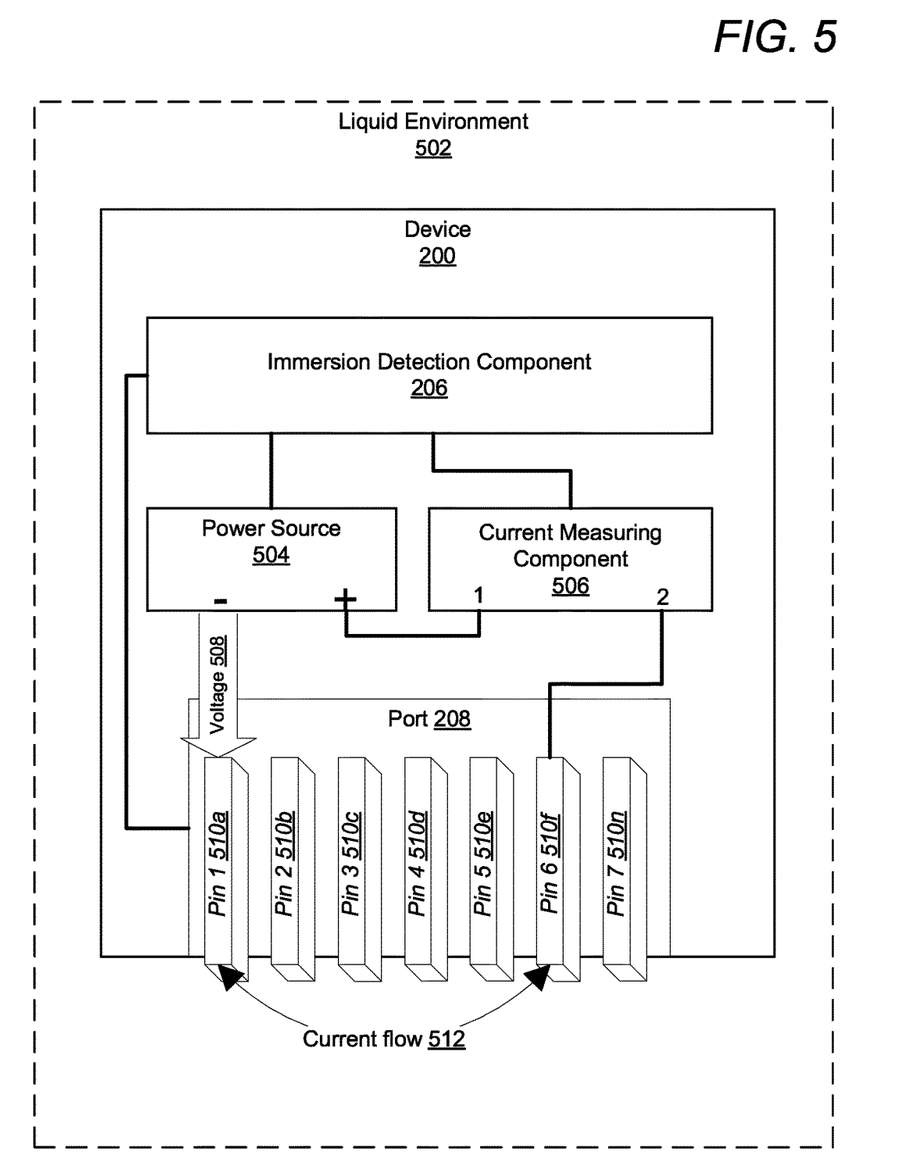
FIG. 5 illustrates a device having a serial port that may be used to measure a level of electrical conductivity of a liquid environment, in accordance with one or more embodiments.

For example, FIG. 5 illustrates device 200 being immersed in liquid environment 502. As illustrated, pins 510a-n of port 208 are exposed to the liquid environment. Current measuring component 506 is connected to both power source 504 and a second pin (pin 510f) of port 208. IDC 206 instructs power source 504 to apply a voltage 508 to a first pin (pin 510a) of port 208. In one embodiment, IDC 206 may instruct power source 504 to apply voltage 508 at regular time intervals, responsive to a user request, and/or responsive to receiving data from a sensor (e.g., an ambient light sensor or proximity sensor). After applying a voltage 508 to a first pin (pin 510a) of port 208, current measuring component 506 then measures current flow 512 between pin 510a (which is connected to the power source) and pin 510f, which is then provided to IDC 206. Based on the measured current flow 512 between pin 510a and pin 510f, IDC 206 calculates a level of electrical conductivity of environment 250. In one embodiment, current measuring component 506 is an ammeter. In another embodiment, power source 504 and/or current measuring component 506 are components of immersion detection component 206.

With reference again to FIG. 2, device 200 also includes barometric altimeter 204, which measures an ambient pressure of environment 250. During immersion of device 200 in a liquid environment, IDC 206 receives pressure measurement 214 (e.g., a barometric pressure hectopascal (hPa) reading) from barometric altimeter 204 and correlates pressure measurement 214 to a particular depth that is representative of a specific depth of device 200 within a liquid environment. The correlation can involve use of a pressure to submerged depth table that is stored within, or accessible by, device 200, in one embodiment. Based on the determined specific depth of device 200, IDC 206 may apply modifications to any of: input devices, output devices, sensors, and software or applications of device 200. Furthermore, IDC 206 may apply different modifications at different measured depths of device 200. For example, IDC 206 may apply a first one or more modifications when the specific depth of device 200 reaches a first threshold (e.g., disable an ambient light sensor of device 200 at a depth of 1 m in the liquid environment) and a second one or more modifications when the specific depth of device 200 reaches a second threshold (e.g. turn off device 200 at a depth of 10 m in the liquid environment). Additionally, IDC 206 may power down select components of device 200 (or shutdown device 200 entirely) as soon as device 200 becomes immersed in a liquid environment or when a specific depth of device 200 reaches a particular depth threshold.

Additionally, in response to determining device 200 is immersed in a liquid environment, IDC 206 may also track an amount of time that has expired since device 200 was immersed in the liquid environment. IDC 206 may apply different modifications at elapsed time thresholds or intervals since device 200 was immersed. That is, IDC 206 may apply a first one or more modifications when the amount of time since device 200 became immersed in the liquid environment reaches a first threshold and a second one or more modifications when the amount of time since device 200 became immersed in the liquid environment reaches a second threshold. For example, IDC 206 may disable a wireless radio of device 200 after the amount of time since device 200 became immersed reaches 10 minutes and/or may power down select components of device 200 (or shutdown device 200 entirely) after the amount of time since device 200 became immersed reaches 1 hour.

In one embodiment, the at least one modification applied to device 200 while device 200 is immersed in a liquid environment may further include one or more modifications to display 210. The one or more modifications to display 210 may include, for example, IDC 206 adjusting a brightness of a backlight of display 210, changing a touch input sensitivity model of a touch screen component of display 210 from capacitive model to a resistive model, and/or changing a minimum amount of pressure required to register a touch actuation in a touch screen component of display 210.

Figure 6A:
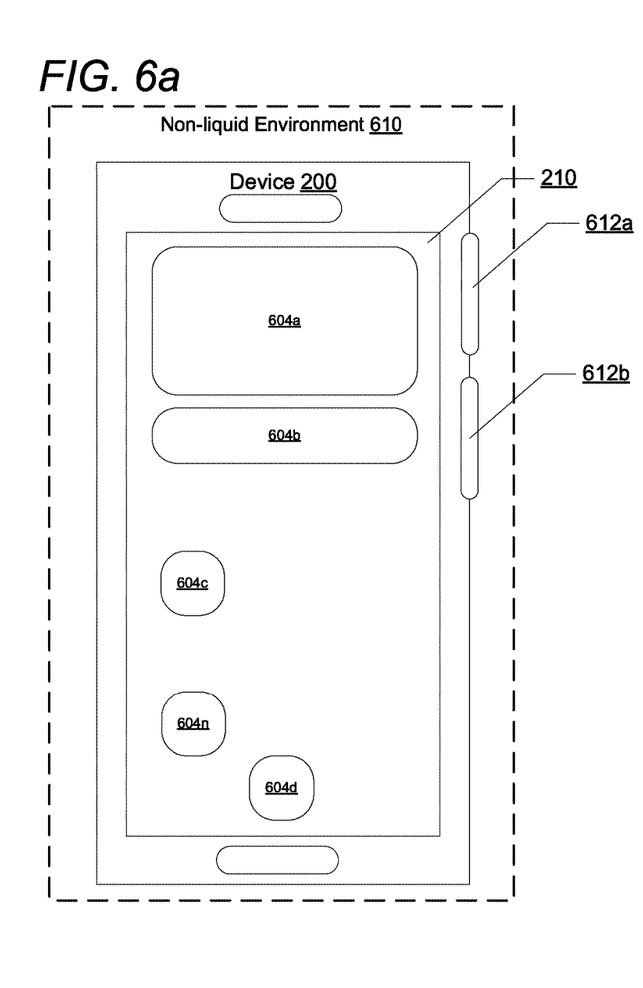
FIG. 6A illustrates an example user interface of a display of a device that is not immersed in a liquid environment, in accordance with one or more embodiments.
Figure 6B:
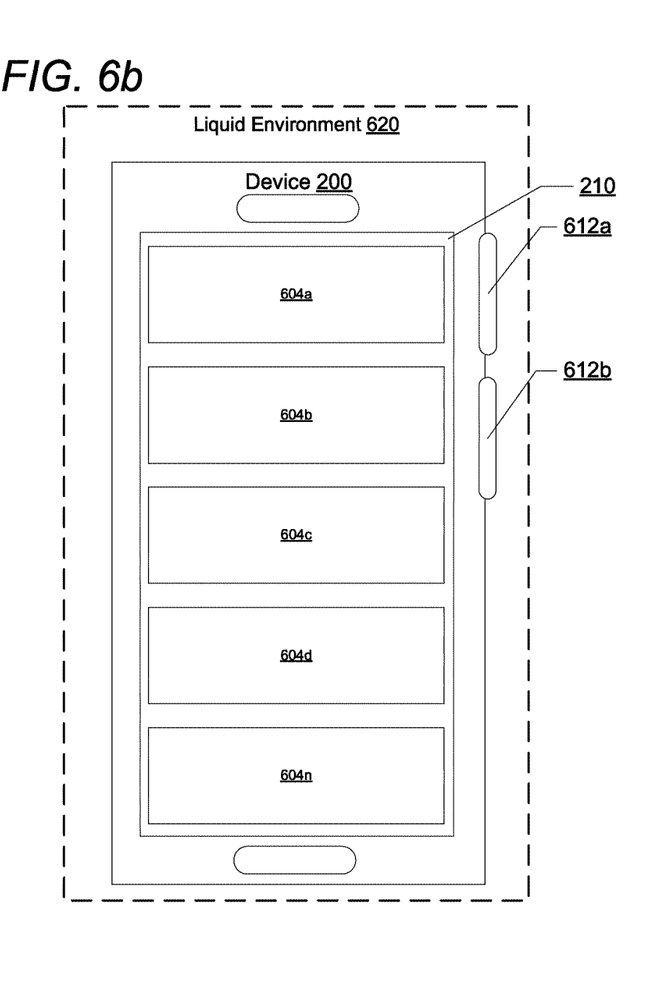
FIG. 6B illustrates an example user interface of a display of a device that is immersed in a liquid environment, in accordance with one or more embodiments.

In another embodiment, the at least one modification that is applied to device 200 while device 200 is immersed in a liquid environment may further include one or more modifications to software user interface 220. The one or more modifications to software user interface 220 may include changes to an arrangement, size, and/or shape of components of a user interface. For example, while immersed in a liquid environment, components and/or icons in a user interface 220 (e.g. a home-screen or desktop interface) may be rearranged and resized from a grid to a vertical list in order to facilitate easier navigation of user interface 220 using hardware buttons of device 200. For example, FIG. 6A illustrates device 200 having a touch screen display 210 that is displaying a user interface having a plurality of objects 604a-n, and which is located within a non-liquid environment 610. Objects 604a-n may include any user interface and/or software components such as, but not limited to, program windows, program icons, links, and text. Objects 604a-n are arranged in a grid and may be interacted with via an input device such as user tactile input to touch screen display 210. As illustrated by FIG. 6B, in response to immersing device 200 in liquid environment 620 (where touch screen display 210 may not properly operate), IDC 206 may automatically apply one or more modifications to the user interface that rearranges and/or resizes objects 604a-n from a grid to a vertical list. Items in the vertical list may be interacted with using touch screen display 210 (if operational in liquid environment 620) and may also be interacted with using volume up 612a and volume down 612b buttons and/or other hardware buttons (not pictured) of device 200.

With reference again to FIG. 2, in another embodiment, in lieu of modifying user interface 200 while device 200 is immersed in a liquid environment, a replacement user interface (not pictured) may be activated that replaces user interface 200. Additionally, the at least one modification may further include one or more changes to the behavior of application 222 of device 200. For example, in response to a first application receiving a notification (e.g., a notification that a new email) from a second application, the second application may be automatically launched rather than simply displaying the notification. In one embodiment, application 222 includes one or more applications, such as applications 116.

In another embodiment, the at least one modification that is applied to device 200 while device 200 is immersed in a liquid environment may further include one or more modifications to a behavior of one or more input components 224. For example, while immersed in a liquid environment, a volume up action and volume down action typically associated with respective volume up and volume down buttons of device 200 may be suspended and a press of the volume up and volume down buttons may instead be used to vertically navigate up and down within a user interface. Additionally, additional actions/behaviors may also be bound to input devices while device 200 is immersed. For example, a particular application may be launched or a particular action may be performed within an application by performing long-press or double press of a volume up button of device 200. As another example, selection or actuation of a highlighted user interface component may be associated with a quick press of a power or camera button of device 200. Additionally, the at least one modification may further include repurposing one or more sensors or input devices to perform a new function. For example, a microphone of device 200 may be repurposed to detect user taps on a housing of device 200, and the user taps may be converted into a user input. Thus, a single tap on a housing of device 200 can be converted to actuation of a highlighted component either in an application 222 or displayed on/in user interface 220. Further still, while immersed in a liquid environment, gyroscopic sensors and accelerometers of device 200 may be used to receive user input via tilting or movement of device 200. For example, a user may move a virtual cursor in application 222 or user interface 220 by tilting device 200 while immersed in a liquid environment. Additionally, while immersed in a liquid environment, a user may actuate a current item that the virtual cursor is located on by tapping the housing of device 200. The tapping is detected by a microphone of device 200, in one embodiment.

In another embodiment, the at least one modification that is applied to device 200 while device 200 is immersed in a liquid environment may further include one or more modifications to the operation of input components 224, output components 226, and sensors 228 of device 200. While immersed in a liquid environment, one or more devices from among input components 224, output components 226, and sensors 228 that are not suitable for operational use in the liquid environment may be disabled. For example, IDC 206 may disable components of device 200 (e.g., a touch screen of display 210 and a proximity sensor or ambient light sensor) that are not configurable for use in the liquid environment in order to prevent false inputs and/or measurements. Similarly, while immersed in a liquid environment, IDC 206 may enable one or more devices from among input components 224, output components 226, and sensors 228 that are only suitable for use in the liquid environment. For example, the barometric altimeter may be enabled only in the liquid environment. In still another embodiment, the operation of input components 224, output components 226, and sensors 228 of device 200 may be further enhanced or modified while device 200 is immersed in a liquid environment. For example, IDC 206 may increase a transmission power of one or more wireless radios (e.g., wireless radios 140a-n) while device 200 is immersed in the liquid environment in order to maintain one or more wireless connections of device 200.

In another embodiment, the at least one modification that is applied to device 200 while device 200 is immersed in a liquid environment may further include one or more modifications to audio subsystems of device 200. For example, while device 200 is immersed in the liquid environment, IDC 206 may also increase and/or decrease speaker output and microphone input levels of device 200. IDC 206 may also apply acoustical filters and/or signal processing to a sound outputted by a speaker or sound input received by a microphone in order to accentuate or mitigate acoustical effects and/or audio artifacts caused by the liquid environment. While device 200 is immersed in the liquid environment, IDC 206 may interpret audio received by a microphone of device 200 as input which may be used, for example, to navigate and/or trigger actions (e.g. take a picture or display/output a current specific depth of device 200) within application 222 or user interface 220.

In another embodiment, the at least one modification that is applied to device 200 while device 200 is immersed in a liquid environment may further include one or more modifications to camera sensor 230 and/or one or more subsystems of camera sensor 230. The one or more modifications to camera sensor 230 may include, for example, adjusting a shutter speed and/or image capture resolution of camera sensor 230. Additionally, the one or more modifications to camera sensor 230 may include applying one or more processing modifications to image data captured by camera sensor 230, such as: noise reduction, exposure modifications, brightness modifications, and color correction and/or white balance modifications. Further still, the one or more modifications to camera sensor 230 may also include modifications to a focus subsystem, including enabling/disabling auto focus or changing characteristics of the focus subsystem, such as a time-of-flight attribute for a laser focus sensor. The one or more modifications to camera sensor 230 may also include modifications to a high dynamic range (HDR) image processing subsystem. For example, in response to IDC 206 detecting that device 200 is immersed in a liquid environment, IDC 206 may modify camera sensor 230 to (1) disable or modify characteristics of an autofocus subsystem, (2) increase a level of brightness filter and noise reduction filter that is applied to captured image data while device 200 is immersed, and (3) decrease a shutter speed of camera sensor 230. In another example, in response to IDC 206 detecting that device 200 is immersed in a liquid environment at a specific depth (e.g., at least 10 meters), the shutter speed of camera sensor 230 is further decreased. Camera sensor 230 may also be used in a liquid environment to detect gestures (e.g., hand motions and movements) by a user which may be translated to user input.

Figure 7:
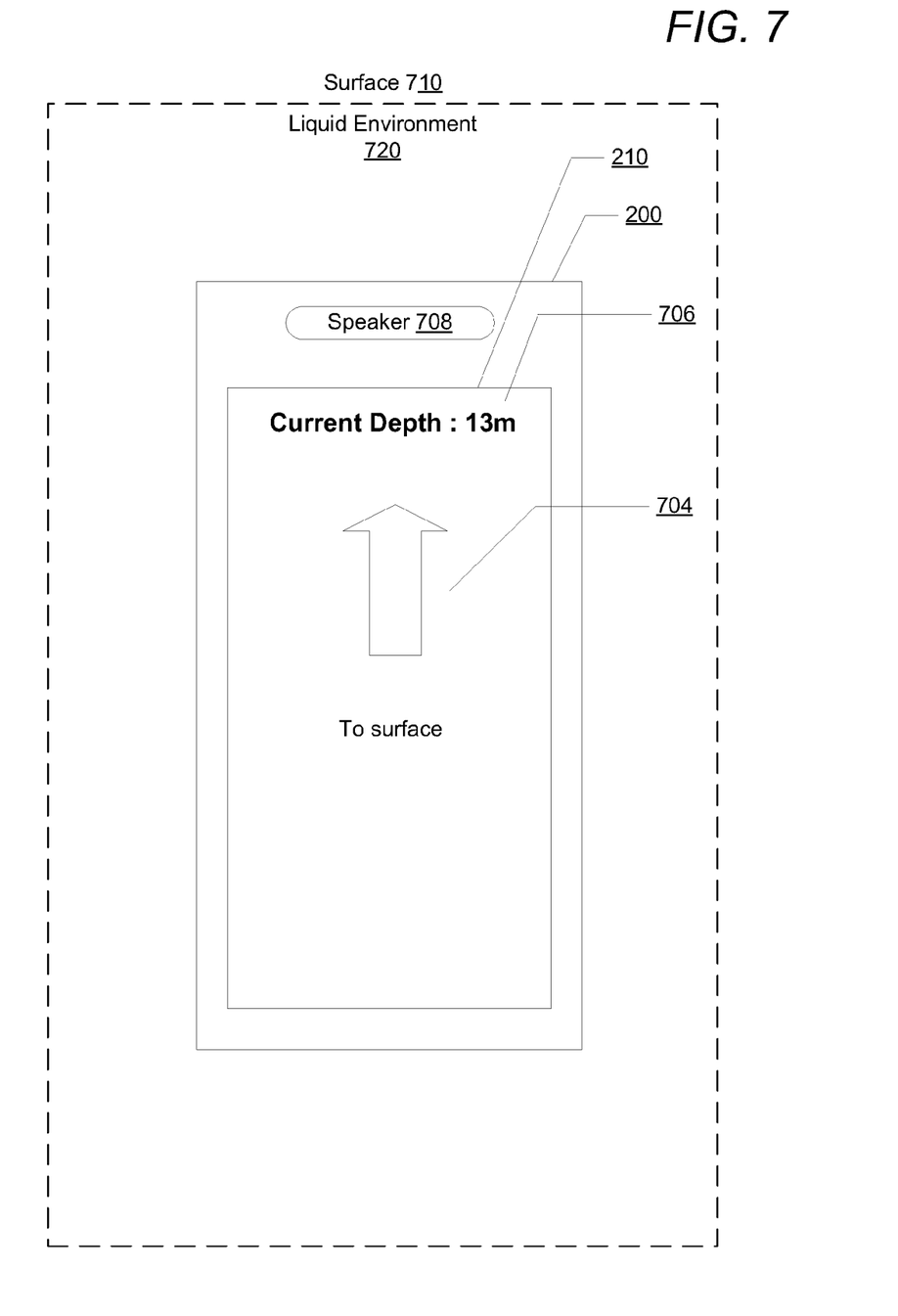
FIG. 7 illustrates a device having a user interface including a buoyant indicator that points to a surface of a liquid environment, in accordance with one or more embodiments.

In one embodiment, while device 200 is immersed, IDC 206 may continually measure the specific depth of device 200 and record all movement that is detected by one or more motion sensors (e.g., gyroscopic sensors and accelerometers) of device 200 in order to calculate, in real-time, a position of device 200 relative to a surface of a liquid environment that device 200 is immersed within. Based on this calculation, IDC 206 calculates, in real-time, a buoyant direction of device 200. As further illustrated by FIG. 7, IDC 206 may render, in real-time, a buoyant indicator 704 on display 210 of device 200 which points in the direction of a surface 710 of a liquid environment 720 that device 200 is immersed within. For example, a user of device 200 that has become disoriented underwater can swim in the direction buoyant indicator 704 points towards in order to reach surface 710 of liquid environment 720. IDC 206 may also render a measurement of a current specific depth 706 on display 210 of device 200. Further still, IDC 206 may also output a spoken measurement of the specific depth via speaker 708 of device 200.

With reference again to FIG. 2, in another embodiment, IDC 206 may also automatically activate a beacon mode that facilitates recovery of device 200 if lost is a liquid environment (e.g. at the bottom of a lake). When beacon mode is activated, IDC 206 may place device 200 in a low-power mode that disables or reduces the functionality of one or more input devices, one or more output devices, and/or one or more sensors of device 200. When beacon mode is activated, IDC 206 may also terminate any unnecessary applications running on device 200. Additionally, in response to activation of beacon mode, IDC 206 may automatically attempt to determine a current location of device 200 and transmit coordinates associated with the current location to another device (e.g., device 152*a* or server 154) via a wireless connection. In another embodiment, in response to activation of beacon mode, IDC 206 may transmit a last known location to another device. In still another embodiment, in response to activation of beacon mode, IDC 206 may capture, using camera sensor 230, an image and/or video of the current surroundings of device 200 and transmit the image and/or video to another device. In one embodiment, IDC 206 may determine a current location of device 200 by using latitude and longitude coordinate information provided to, or measured by, device 200. In another embodiment, IDC 206 may detect the current location of device 200 using a GPS sensor or by triangulating a cellular network signal using one or more wireless radios of device 200.

During beacon mode, IDC 206 may also periodically activate one or more output devices or sensors to assist in the recovery of device 200. For example, a camera flash (e.g., flash 146) or display 210 may periodically be briefly illuminated and/or a speaker of device 206 may periodically broadcast a sound effect. Additionally, IDC 206 may disable one or more wireless radios of device 200 during beacon mode in order to minimize a power consumption of the wireless radios. IDC 206 may then only periodically activate the wireless radios in an attempt to detect and/or connect to a nearby network and/or device. The beacon mode may automatically be activated by IDC 206. For example, beacon mode may be autonomously activated in response to a specific depth of device 200 reaching a threshold limit and/or responsive to IDC 206 determining that no user input has been received and/or no movement has been detected by device 200 for a pre-established amount of time.

It should be noted that in one or more embodiments, any of the above modifications may be automatically applied in response to IDC 206 detecting a specific condition (e.g., the device being immersed in (or removed from) a liquid environment or the specific depth reaching 10 meters). In an alternate embodiment, any of the above modifications may be enabled by a user of device 200 at any time. Additionally, any of the above modifications may also be manually disabled and/or reverted by a user of device 200 at any time, including while device 200 is still immersed in a liquid environment.

Figure 3:
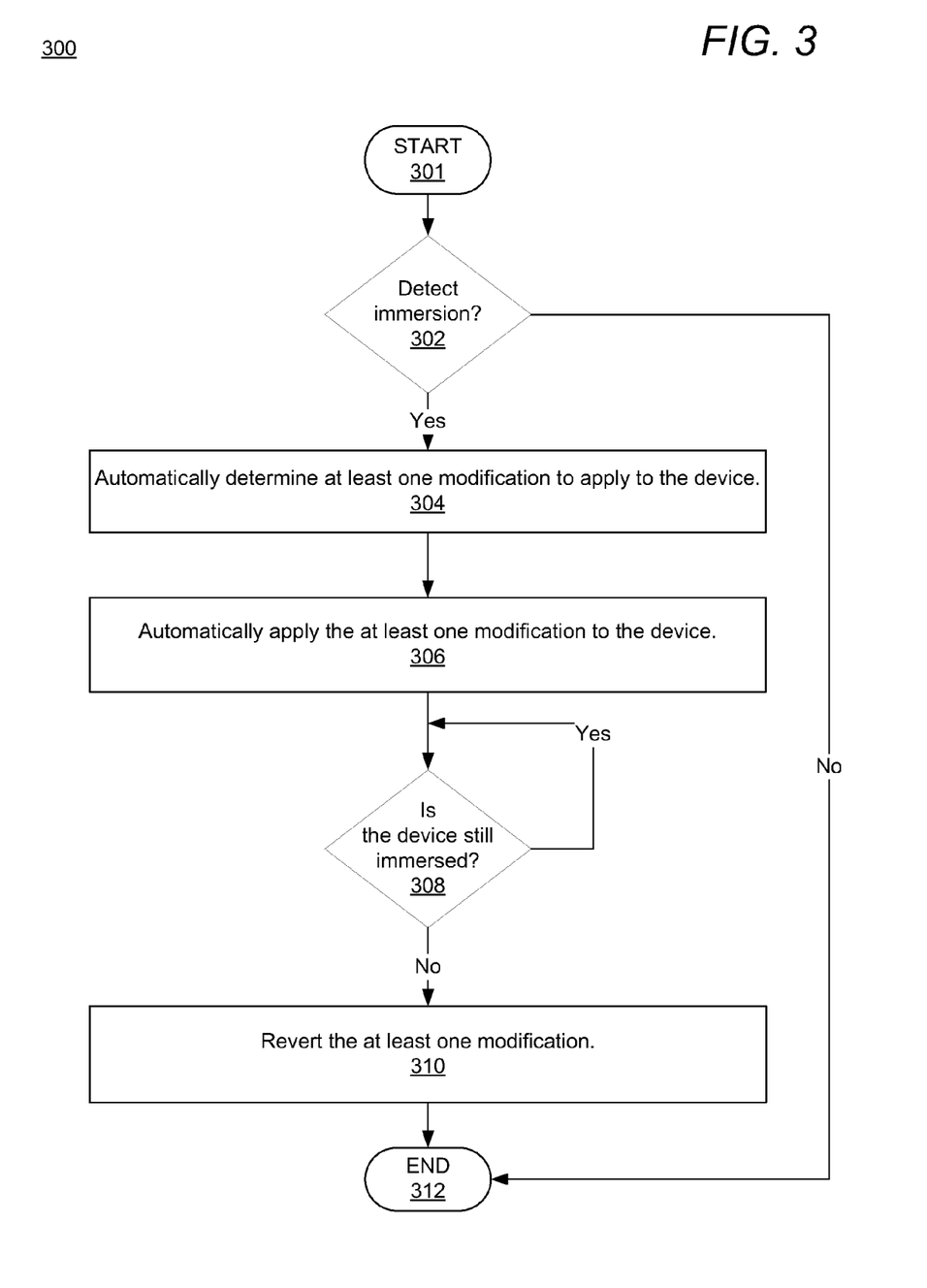
FIG. 3 is a flow chart illustrating a method for automatically applying one or more modifications to a device that enable specific device functionality while the device is immersed in the liquid environment, in accordance with one or more embodiments.
Figure 4:
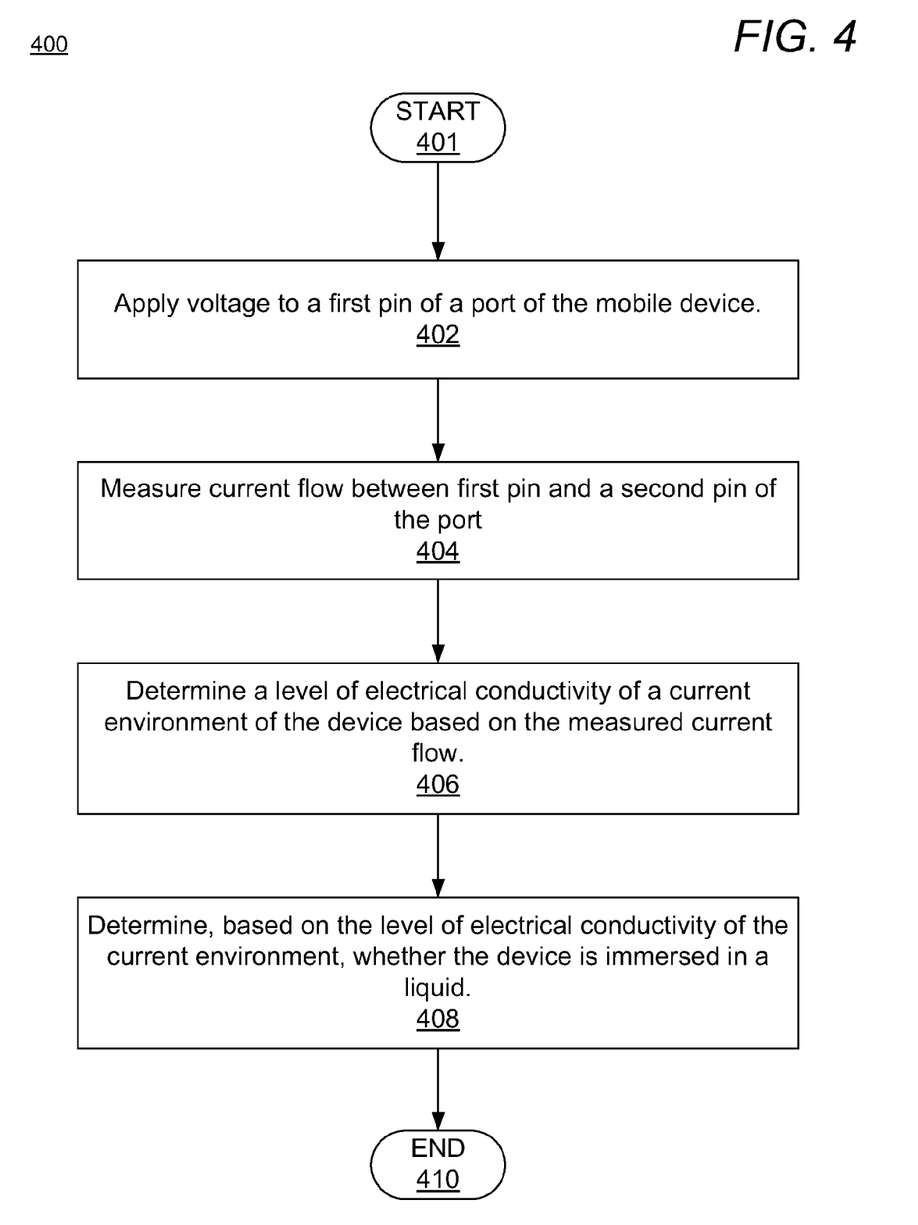
FIG. 4 is a flow chart illustrating a method for determining whether a device is immersed in a liquid by calculating a level of electrical conductivity of a current environment of the device, in accordance with one or more embodiments.

Referring now to FIGS. 3-4, there are illustrated flow charts of various methods for, in response to determining a device is immersed in a liquid, automatically applying one or more modifications to the device that enable specific device functionality while immersed in the liquid environment, according to one or more embodiments. Aspects of the methods are described with reference to the components of FIGS. 1-2. Several of the processes of the methods provided in FIGS. 3-4 can be implemented by CPU 104 or IDC 206 executing software code of IDRU 118 within a mobile device or generic data processing system, respectively. For simplicity, the methods described below are generally described as being performed by IDC 206 of device 200.

Referring now to FIG. 3, there is depicted a high-level flow-chart illustrating a method for automatically applying one or more modifications to a device that enable specific device functionality while the device is immersed in a liquid environment, in accordance with one or more embodiments of the present disclosure. Method 300 commences at initiator block 301 and proceeds to block 302 at which point IDC 206 detects whether device 200 is immersed in a liquid environment. In one embodiment, IDC 206 receives an indication from a sensor of device 200 that indicates whether device 200 is immersed in a liquid environment. In another embodiment, IDC 206 calculates an electrical conductivity of the environment to determine whether device 200 is immersed in a liquid environment. In response to IDC 206 detecting that device 200 is not immersed in a liquid environment, the process terminates at block 312.

In response to IDC 206 detecting that device 200 is immersed in a liquid environment, the method continues to block 304 and IDC 206 automatically determines at least one modification to apply to device 200. At block 306, IDC 206 applies the at least one modification to device 200. IDC 206 then determines whether the device is still immersed in the liquid environment (block 308). In response to determining the device is no longer immersed in the liquid environment, the method continues to block 310 where the at least one modification previously applied to device 200 is reverted. Alternatively, the at least one modification may be applied to the device until an input is received that instructs IDC 206 to revert the at least one modification. The method then terminates at block 312.

Referring now to FIG. 4, there is depicted a high-level flow-chart illustrating a method for determining whether a device is immersed in a liquid by calculating a level of electrical conductivity of an environment of the device, in accordance with one or more embodiments of the present disclosure. Method 400 commences at initiator block 401. At block 402, IDC 206 applies a voltage to a first pin of a port of a device. At block 404, IDC 206 measures a current flow between the first pin and a second pin of the port. The method continues to block 406 where IDC 206 determines and/or calculates a level of electrical conductivity of the environment of the device based on the measured current flow through the environment from the first pin to the second pin. IDC 206 then determines, based on the calculated level of electrical conductivity of the current environment, whether the device is immersed in a liquid environment (block 408). IDC 206 can also determine, based on the level of electronic conductivity measured, specific characteristics of the liquid environment, such as whether the liquid is salt water or fresh water, etc. The method then terminates at block 410.

In the above-described flow charts, one or more of the method processes may be embodied in a computer readable device containing computer readable code such that a series of steps are performed when the computer readable code is executed on a computing device. In some implementations, certain steps of the methods are combined, performed simultaneously or in a different order, or perhaps omitted, without deviating from the scope of the disclosure. Thus, while the method steps are described and illustrated in a particular sequence, use of a specific sequence of steps is not meant to imply any limitations on the disclosure. Changes may be made with regards to the sequence of steps without departing from the spirit or scope of the present disclosure. Use of a particular sequence is therefore, not to be taken in a limiting sense, and the scope of the present disclosure is defined only by the appended claims.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. Computer program code for carrying out operations for aspects of the present disclosure may be written in any combination of one or more programming languages, including an object oriented programming language, without limitation. These computer program instructions may be provided to a processor of a general purpose computer, special purpose computer, or other programmable data processing apparatus to produce a machine that performs the method for implementing the functions/acts specified in the flowchart and/or block diagram block or blocks. The methods are implemented when the instructions are executed via the processor of the computer or other programmable data processing apparatus.

As will be further appreciated, the processes in embodiments of the present disclosure may be implemented using any combination of software, firmware, or hardware. Accordingly, aspects of the present disclosure may take the form of an entirely hardware embodiment or an embodiment combining software (including firmware, resident software, micro-code, etc.) and hardware aspects that may all generally be referred to herein as a "circuit," "module," or "system." Furthermore, aspects of the present disclosure may take the form of a computer program product embodied in one or more computer readable storage device(s) having computer readable program code embodied thereon. Any combination of one or more computer readable storage device(s) may be utilized. The computer readable storage device may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage device would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage device may be any tangible medium that can contain, or store a program for use by or in connection with an instruction execution system, apparatus, or device.

While the disclosure has been described with reference to example embodiments, it will be understood by those skilled in the art that various changes may be made and equivalents may be substituted for elements thereof without departing from the scope of the disclosure. In addition, many modifications may be made to adapt a particular system, device, or component thereof to the teachings of the disclosure without departing from the scope thereof. Therefore, it is intended that the disclosure not be limited to the particular embodiments disclosed for carrying out this disclosure, but that the disclosure will include all embodiments falling within the scope of the appended claims.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method comprising:
    detecting, via an immersion detection component (IDC) of an electronic device, immersion of the device in a liquid environment;
    in response to detecting the immersion of the device in the liquid environment:
        automatically determining, via the IDC, at least one first modification that can be applied to the device to at least one of enable specific device functionality that facilitates operation of the device in the liquid environment or disable specific device functionality, including disabling one or more components that are not configurable for operational use in the liquid environment, while the device is immersed in the liquid environment, the at least one first modification being applied to at least one of input devices, output devices, sensors, software, or applications of the electronic device; and
        automatically applying the at least one modification to the device; and
    in response to detecting that the device is no longer immersed in the liquid environment, reverting the at least one modification.

2. The method of claim 1, wherein detecting immersion of the device in the liquid environment further comprises:
    applying a voltage to a first pin of a port of the device, wherein the port is one of an input port, an output port, and an input/output port;
    measuring a flow of current between the first pin and a second pin of the port;
    determining a level of electrical conductivity of a current environment of the device based on the measured flow of current; and
    determining, based on the level of electrical conductivity of the current environment, whether the device is immersed in the liquid environment.

3. The method of claim 1, wherein: the electronic device includes at least one input device with associated input functions; and automatically determining the at least one modification further comprises:
    determining whether the device includes at least one first input component that is reconfigurable to receive input while the device is immersed in the liquid environment;
    in response to determining that the device includes the at least one first input component, applying the at least one modification to the at least one first input component to enable the at least one first input component to receive input while the device is immersed in the liquid environment;
    determining whether the device includes at least one second input component that is not configured to receive input while the device is immersed in the liquid environment; and
    in response to determining the device includes the at least one second input component, disabling the at least one second input component while the device is in the liquid environment.

4. The method of claim 1, wherein automatically determining the at least one modification further comprises:
    determining whether the device includes at least one first component that is reconfigurable to function while the device is immersed in the liquid environment, wherein the at least one first component includes at least one of an output component and a sensor;
    in response to determining the device includes the at least one first component, applying the at least one modification to the at least one first component to enable the at least one first component to function while the device is immersed in the liquid environment;
    determining whether the device includes at least one second component that is not configured to function while the device is immersed in the liquid environment, wherein the at least one second component includes at least one of an output component and a sensor; and
    in response to determining the device includes the at least one second component, disabling the at least one second component while the device is immersed in the liquid environment.

5. The method of claim 1, further comprising:
    in response to detecting the immersion of the device in the liquid environment, tracking an amount of time the device has been immersed in the liquid environment; and
    triggering the at least one modification in response to the device being immersed in the liquid environment for more than a pre-determined time threshold.

6. The method of claim 1, further comprising:
    in response to detecting the immersion of the device in the liquid environment, modifying at least one of a size, a shape, an arrangement, a function, and a position of at least one component of a viewable user interface of the device to facilitate use while the device is immersed in the liquid environment, wherein the modified user interface is displayed and viewable on a display of the device while the device is immersed in the liquid environment.

7. The method of claim 1, further comprising:
    determining, via a barometric altimeter of the device, a pressure measurement in the liquid environment; and
    calculating, in real-time, a specific depth of the device within the liquid environment, based on the pressure measurement; and
    applying the at least one modification to the device is based on the calculated real-time specific depth, wherein different modifications can be applied at different measured depths of the electronic device.

8. The method of claim 1, further comprising:
    in response to detecting the immersion of the device in the liquid environment, performing at least one modification to at least one image sensor of the device from among:
        at least one first modification to a focus subsystem of the at least one image sensor;
        at least one second modification to a capture subsystem of the at least one image sensor; and
        at least one third modification that changes an actuation trigger for at least one shutter of the at least one image sensor, wherein the actuation trigger causes the at least one shutter to capture image data.

9. A device comprising:
    an immersion detection component that detects an immersion of the device in a liquid environment;
    at least one input/output (I/O) component having associated I/O functions; and
    a processor communicatively coupled to the immersion detection component and the I/O components and which receives a signal from the immersion detection component identifying when the device is immersed in the liquid environment, the processor executing an immersion response firmware, wherein:

in response to receiving the signal identifying that the device is immersed in the liquid environment:
  automatically determines at least one first modification to apply to the device to at least one of enable specific device functionality that facilitates operation of the device in the liquid environment or disable specific device functionality, including disabling one or more components that are not configurable for operational use in the liquid environment, while the device is immersed in the liquid environment, the at least one first modification being applied to at least one of input devices, output devices, sensors, software, or applications of the electronic device; and
  the processor automatically triggers the at least one modification to the device; and
in response to the immersion detection component detecting that the device is no longer immersed in the liquid environment, the processor reverts the at least one modification.

10. The device of claim 9, further comprising:
a port having a plurality of pins, wherein the port is one of an input port, an output port, and an input/output port;
a power supply;
wherein the immersion detection component is electrically connected to the power supply and the port and, to detect immersion of the device, the immersion detection component:
  applies a voltage to a first pin of the plurality of pins; and
  measures a flow of current between the first pin and a second pin of the port; and
in response to the immersion detection component measuring the flow of current between the first pin and the second pin:
  the processor determines a level of electrical conductivity of a current environment of the device, based on the flow of current between the first pin and the second pin; and
  the processor determines, based on the level of electrical conductivity of the current environment, whether device is immersed in the liquid environment.

11. The device of claim 9, further comprising:
at least one first input component that is reconfigurable to receive input while the device is immersed in the liquid environment;
at least one second input component that is not configured to receive input while the device is immersed in the liquid environment; and
in response to the immersion detection component detecting the immersion of the device in the liquid environment:
  the processor triggers the at least one modification to the at least one first input component to enable the at least one first input component to receive input while the device is immersed in the liquid environment; and
  the processor disables the at least one second input component.

12. The device of claim 9, further comprising:
at least one first component that is reconfigurable to function while the device is immersed in the liquid environment, wherein the at least one first component includes at least one of an output component and a sensor;
at least one second component that is not configured to function while the device is immersed in the liquid environment, wherein the at least one second component includes at least one of an output component and a sensor; and
in response to the immersion detection component detecting the immersion of the device in the liquid environment:
  the processor applies the at least one modification to the at least one first component to enable the at least one first component to function while the device is immersed in the liquid environment; and
  the processor disables the at least one second component.

13. The device of claim 9, further comprising, in response to detecting the immersion of the device in the liquid environment:
the processor tracks an amount of time the device has been immersed in the liquid environment; and
the processor triggers the at least one modification in response to the device being immersed in the liquid environment for more than a pre-determined time threshold.

14. The device of claim 9, further comprising:
a display communicatively coupled to the processor; and
in response to the immersion detection component detecting the immersion of the device in the liquid environment, the processor modifies at least one of a size, a shape, an arrangement, a function, and a position of at least one component of a viewable user interface of the device to facilitate use while the device is immersed in the liquid environment, wherein the modified user interface is displayed and viewable on the display while the device is immersed in the liquid environment.

15. The device of claim 9, further comprising:
a barometric altimeter communicatively coupled to the processor; and
in response to the immersion detection component detecting the immersion of the device in the liquid environment:
  the processor receives a pressure measurement in the liquid environment from the barometric altimeter; and
  the processor calculates, in real-time, a specific depth of the device within the liquid environment, based on the pressure measurement; and
  the processor applies the at least one modification to the device is based on the calculated real-time specific depth, wherein different modifications can be applied at different measured depths of the electronic device.

16. The device of claim 9, further comprising:
at least one image sensor communicatively coupled to the processor; and
in response to the immersion detection component detecting the immersion of the device in the liquid environment, the processor applies at least one modification to the at least one image sensor of the device from among:
  at least one first modification to a focus subsystem of the at least one image sensor;
  at least one second modification to a capture subsystem of the at least one image sensor; and
  at least one third modification that changes an actuation trigger for at least one shutter of the at least one image sensor, wherein the actuation trigger causes the at least one shutter to capture image data.

17. A computer program product comprising:
a non-transitory computer readable storage device; and program code on the computer readable storage device that when executed within a processor associated with a device having an immersion detection component (IDC) and input/output (I/O) devices with associated I/O functions, the program code enables the device to provide the functionality of:

receiving a first indication from the IDC that the device is immersed in a liquid environment;

in response to receiving the first indication:

automatically determining at least one first modification that can be applied to the device to at least one of enable specific device functionality that facilitates operation of the device in the liquid environment or disable specific device functionality, including disabling one or more components that are not configurable for operational use in the liquid environment, while the device is immersed in the liquid environment, the at least one first modification being applied to at least one of input devices, output devices, sensors, software, or applications of the electronic device; and automatically applying the at least one modification to the device;

receiving a second indication that the device is no longer immersed in the liquid environment; and in response to receiving the second indication, reverting the at least one modification.

18. The computer program product of claim 17, wherein the program code for detecting immersion of the device in the liquid environment further comprises code that enables the device to provide the functionality of:

triggering an immersion detection module to apply a voltage to a first pin of a port of the device, wherein the port is one of an input port, an output port, and an input/output port;

triggering the immersion detection module to measure a flow of current between the first pin and a second pin of the port;

determining a level of electrical conductivity of a current environment of the device based on the measured flow of current; and determining, based on the level of electrical conductivity of the current environment, whether the device is immersed in the liquid environment.

* * * * *